(12) United States Patent
Nilsson

(10) Patent No.: US 6,298,115 B1
(45) Date of Patent: Oct. 2, 2001

(54) METHOD FOR CALIBRATING A DETECTOR MEANS

(75) Inventor: Görgen Nilsson, Storvreta (SE)

(73) Assignee: Scanditronix Medical AB, Uppsala (SE)

(*) Notice: Subject to any disclaimer, the term of this patent is extended or adjusted under 35 U.S.C. 154(b) by 0 days.

(21) Appl. No.: 09/482,112

(22) Filed: Jan. 13, 2000

(51) Int. Cl.[7] .................................. A61N 5/10
(52) U.S. Cl. .............................. 378/65; 378/207
(58) Field of Search ...................... 378/65, 207

(56) References Cited

U.S. PATENT DOCUMENTS

| | | |
|---|---|---|
| 5,511,549 | 4/1996 | Legg et al. . |
| 5,754,622 | 5/1998 | Hughes . |

FOREIGN PATENT DOCUMENTS 0 773 042 A2   5/1997   (EP) .

OTHER PUBLICATIONS

H. Keller et al., "Calibration of a portal imaging device for high-precision dosimetry: A Monte Carlo study," Med. Phys. 25 (Oct. 10, 1998, pp. 1891–1901.

Primary Examiner—Craig E. Church
(74) Attorney, Agent, or Firm—Young & Thompson

(57) ABSTRACT

The present invention relates to a method for calibrating a detector means intended for use in an apparatus for radiotherapy, characterised in that it comprises the steps of placing a patient in the radiotherapy apparatus with the part of the patient to be treated between a radiation emitting device and the detector means, applying a number of detectors on the patient, radiating the patient and the detectors, measuring the emitted radiation with the detectors in order to quantify the radiation dose, detecting the radiation emitted and passed through the patient by the detector means, whereby the detector means comprises a plurality of radiation detectors arranged as to detect the radiation beam, determining the value of the detected radiation from the detectors of the detector means, and relating the value of the detecting means with the measured radiation dose, thereby quantifying the radiation detected by the detector means.

13 Claims, 2 Drawing Sheets

METHOD FOR CALIBRATING A DETECTOR MEANS

TECHNICAL FIELD

The present invention relates to a method for calibrating a detector means intended for use in an apparatus for radiotherapy.

BACKGROUND OF THE INVENTION

Radiotherapy has been used for treating cancer in the human body since early 1900. Even though radiation of cancer tumours is known to be efficient, mortality rate for many cancers remained virtually unchanged for a long time. The major cause to this has been the inability to control the primary tumour or the occurrence of metastases. Only by improving the local control may the treatment be more effective.

Therefor the radiotherapy methods and devices have developed in the that sense the energy levels of the radiation accelerators have increased, introduction of collimators in order to shield off and direct the radiation to desired areas, to detect the size and location of the tumour in the patient and to calculate the required dose in dependence of the detection.

Further measures for improving the control are In Vivo dosimetry and Portal image systems. In In Vivo dosimetry the radiated dose is measured outside the human body to verify the delivered dose during treatment. The aim of the In Vivo dosimetry is in most cases to predict the dose inside the body while measuring the dose on the outside. Certain corrections need therefor be made of the detected signal. Conventionally In Vivo dosimetry is used in TBI (Total Body Irradiation) and to verify fraction doses in fractional treatment. This is often done during the first fraction and maybe a few subsequent fractions, i.e. every sixth fraction. The aim is then to verify the predicted dose to the patient and to reduce the number of errors, systematic and/or stochastic, and predict the accumulated dose to the patient if it is applied at each treatment fraction and thereby increase the outcome of the treatment.

The main reasons why general In Vivo dosimetry is not performed frequently are that the detector shields parts of the treatment area of the patient, thereby reducing the dose and in turn the tumour control, and the time and patient flow since it is rather time consuming to apply the detectors onto the patient for each fraction.

The main purpose for the use of Portal Imaging is to verify the position of the patient, either during treatment or afterwards. Traditionally a radiographic film has been placed where the radiation beam exits the patient for exposure during one field at one fraction. The image on the film is then used to verify the position of the patient compared to the treatment plan. In recent years it has become common to use Electronic Portal Imaging (EPI) devices to achieve instant information of the patient positioning.

One problem with the method of measuring only at the first fraction, or at a few fractions, and then rely on those values at the other fractions is that the accelerator of the radiation device is somewhat unstable, i e the output from the accelerator may vary in time due to many factors. Thus, it is not certain that the dose level delivered and measured is the same throughout all fractions, providing uncertainty in the treatment.

Because of that, Portal imaging and in particular EPI has been proposed for In Vivo dosimetry. However there are important limitations using those devices for dosimetry as regards to e g energy dependency, dose rate dependency, dependency in distance to patient etc., primarily since these devices were developed for image capturing and processing and not for dose level detection and measurement.

A few attempts have been made to explore if the optical density of a portal image film could be used as a measure of the relative exit dose. One such research report is disclosed in the publication Radiotherapy and Oncology 29 (1993) 336–340, by C. Fiorino et al. In the report different phantoms have been radiated, the exit dose measured by an ionization chamber and the dose captured on the film. The conclusion of the research is that a good agreement has been found between measured and calculated dose profiles on one hand and optical density profiles on the film on the other hand for different phantoms.

One major problem with the use of a portal imaging device as a measure of the relative dose as described above, is to implement it clinically. The exit dose when treating a human body is very different from radiating a phantom, so corrections have to be calculated in order for the optical density profiles obtained during treatment to correspond to those obtained with the phantom. The uncertainty of the corrections, depending very much on the anatomy of the actual patient and the location of the beam during treatment, implies that there is a large amount of uncertainty in the values obtained from the portal image device.

BRIEF DESCRIPTION OF THE INVENTION

The aim of the invention is to combine the information obtained with In Vivo dosimetry with a detector means able of detecting the radiation beam, when it has passed the body of a treated patient, such as portal imaging device, in order to firstly calibrate the value obtained from the detector means with the In Vivo dosimetry information, and then verify the radiation dose with the detector means, all during treatment of a patient.

According to one aspect of the invention according to the preamble of the description this is achieved by a method for calibrating a detector means intended for use in an apparatus for radiotherapy, characterised in that it comprises the steps of placing a patient in the radiotherapy apparatus with the part of the patient to be treated between a radiation emitting device and the detector means, applying a number of detectors on the patient, radiating the patient and the detectors, measuring the emitted radiation with the detectors in order to quantify the radiation dose, detecting the radiation emitted and passed through the patient by the detector means, whereby the detector means comprises a plurality of radiation detectors arranged as to detect the radiation beam as seen in a cross section of the beam, determining the value of the detected radiation from the detectors of the detector means, and relating the value of the detecting means with the measured radiation dose, thereby quantifying the radiation detected by the detector means.

According to another aspect of the invention it is characterised in that the mean value of the signals from the detectors of the detector means is determined.

Preferably a portal image device, in most cases already included in a radiotherapy device, is used as an image recorder. With the method according to the invention both film and electronic means may be employed.

With the method of the invention a cost effective and reliable method for verifying the dose delivered to the patient is obtained. During the first fraction in a treatment the image recorder is calibrated with the In Vivo dosimetry.

During the subsequent fractions information regarding doe levels may be derived from the image recorder with the help of the image recorder. Since a portal image device is included in radiotherapy devices, a suitable software for determining the radiation beam area to be used and calculating the mean value from the signals of the detectors of that area is the only means that has to be included or invested in, of course apart from an In Vivo dosimetry system.

As compared to earlier attempts of using portal imaging devices as In Vivo devices, no major corrections, leading to uncertainty, need to be performed since the calibration is performed together with the actual patient, which calibration is used only for that patient during fractions for verifying the dose. Because the mean value is used, small differences between fractions in parts of the beam area detected is reduced. With the method it has been found that a sufficiently good correspondence between the measured dose and the calculated value derived from the image contrast is obtained.

These and other aspect on and advantages with the invention will be evident form the detailed description and the accompanying patent claims.

BRIEF DESCRIPTION OF THE DRAWINGS

In the following detailed description of an embodiment if the invention, reference will be made to the drawings, of which

DETAILED DESCRIPTION OF EMBODIMENT

Figure 1:
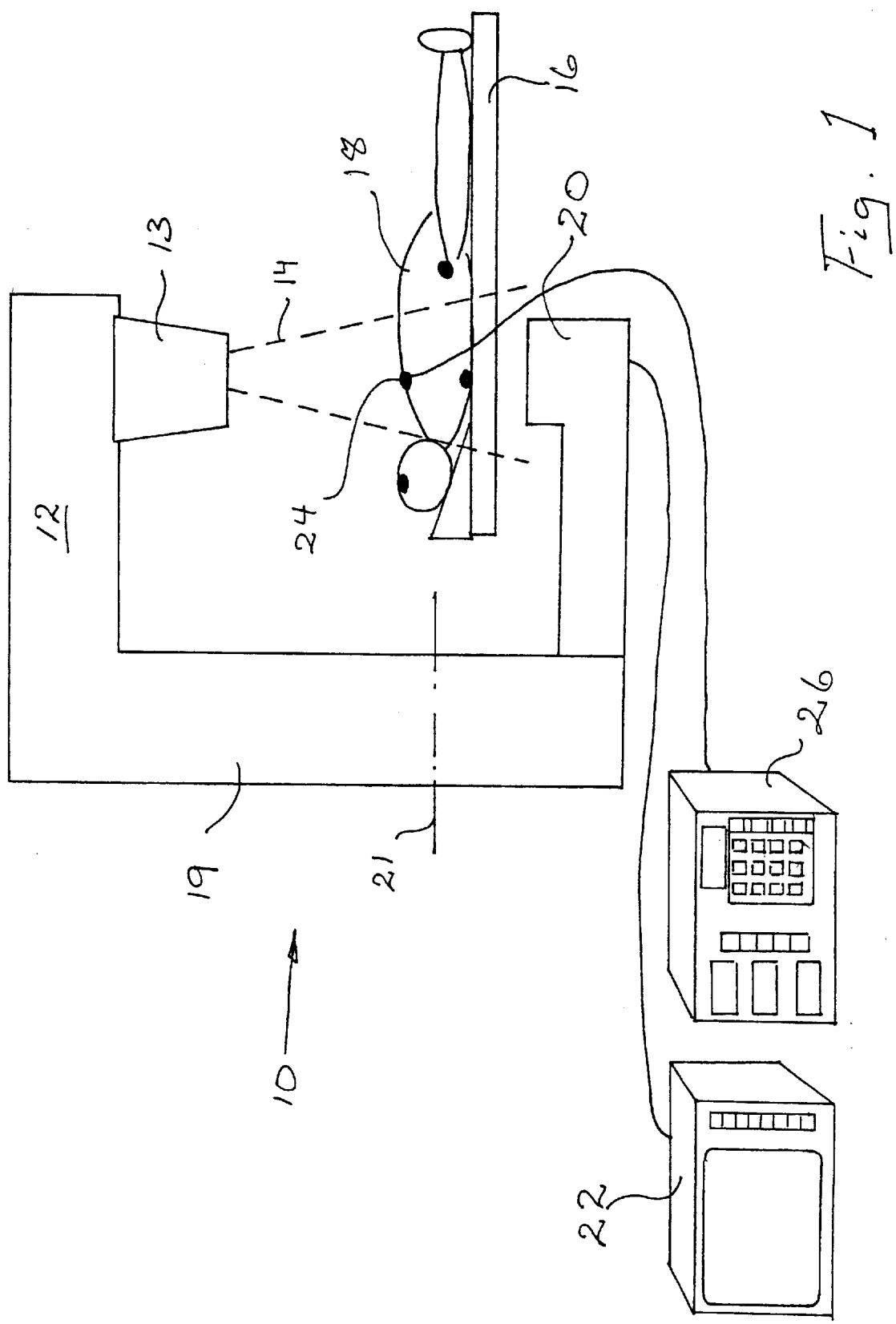
FIG. 1 shows a diagrammatic figure of a radiotherapy device to which the method according to the invention is employed.

A radiotherapy device utilised for treating tumours with radiation is generally denoted with reference numeral 10. The device comprises radiotherapy system 12 capable of emitting a beam 14 of electrons or photons from a treatment head 13. The radiotherapy system may be provided with field-shaping device for allowing the lateral shape of the beam to be altered so as to shield off non-affected areas of the body and concentrate the beam to the tumour. Control means (not shown) are provided for the radiotherapy system.

A table 16 is arranged for a patient 18 to lie on. The table is rotatable around a vertical axis, and movable horizontally and vertically in order to place the area to be treated of the patient in the area of the beam. The treatment head is arranged on a gantry 19, which is rotatable around a horizontal axis 21. To the gantry a portal image device 20 is arranged, positioned opposite the treatment head with the table between them. In the embodiment shown the portal image device is electronic. The portal image device is connected to a control and display device 22.

When planning a treatment of a patient a series of measurements and investigations are performed in order to locate the exact position of the tumour in the body and its size. From this information a treatment plan is formed in which calculations are made on the dose level required, treatment angles, blocking of fields and such, in order to give the required doses to the tumour and to protect risk organs or avoid skeleton parts or the like.

During the first fraction, or one of the first fractions, detectors 24 are placed on the skin of the patient in the area where the radiation beam hits the patient. Detectors may also be placed on other parts of the body inside the primary field or in regions sensitive to radiation in order to verify that they are not exposed to radiation. The detectors 24 on the surface are ones used in In Vivo dosimetry. They may be of semiconductor, thermoluminescent or other type of In Vivo detector, which are known per se. The detectors are connected to a control device 26 for treating the signals from the detectors.

The radiation will enter the body of the patent and irradiate the tumour. The radiation will also pass through the body and hit the portal image device, thus creating an image, from which image the patients position, in relation to the beam can be evaluated in order to verify that the beam is directed mainly at the tumour and not surrounding tissue.

The radiation hitting the portal image device provides a change on the image; density if film is used and signal if an electronic device is used. It has been found that the change is proportional to the actual dose level with a correction factor. Depending on the type of image capturing device used, film or electronic, the average density or average signal respectively is related to the signal detected from the In Vivo detector. In most cases, when film is used, the captured image is digitalized by converting the density to electric signals, for subsequent analysis and use in accordance with the present invention. Therefor, the term signal will be used for both film and electronic device in the following.

Figure 2:
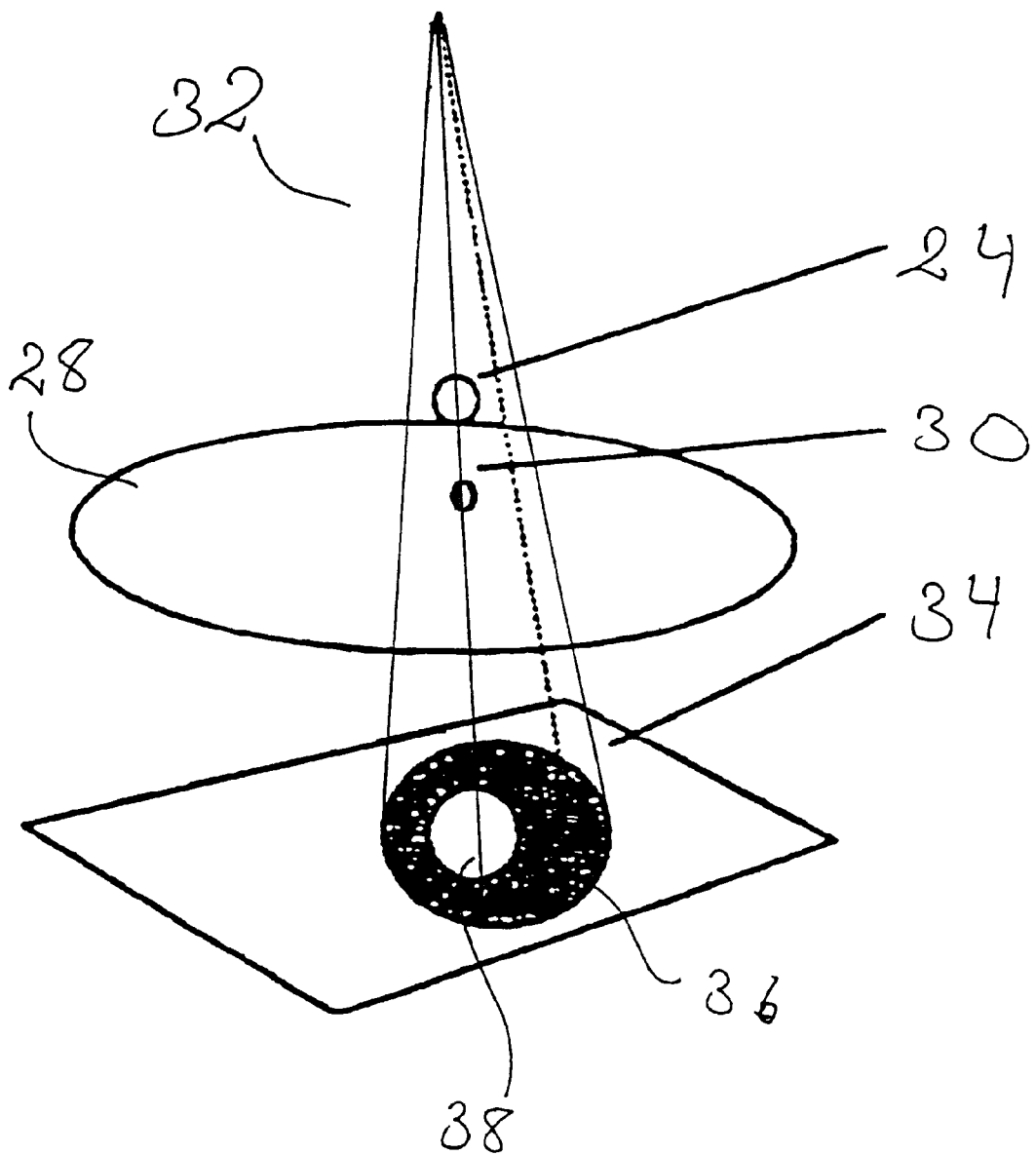
FIG. 2 shows a schematic representation of calibrating an image on the portal image display by using In Vivo dosimetry.

FIG. 2 shows schematically how this is utilised. Reference number 28 indicates a patient's body, number 24 an In Vivo detector, number 30 dose prediction point (tumour), number 32 radiation beam and number 34 portal imaging device (film or EPI). The black area 36 constitutes the radiation beam area on the imaging device and the white spot 38 in the middle the shadowing by the detector.

A calibration factor is calculated from the radiation beam area as:

$$Cal = \frac{D \cdot n}{\sum_{i=1 \to n} S_i}$$

where D is the dose measured by the detector, $S_i$ is the net signal per pixel, i.e. the signal corrected from noise or the like, and n is the number of measuring points in the radiation beam area 36 except from the shadowed area 38. The formula shows that the mean value of the signals from the area forms a calibration factor.

With the calibration factor the portal image device can be used in subsequent fractions without In Vivo dosimetry. The dose at the prediction point is then calculated as:

$$\text{Dose} = Cal \cdot \sum_{i=1 \to n} \frac{S_i}{n}$$

What is obtained is thus a proportional relation between the dose at the prediction point and the mean value from the portal imaging device. The mean value from the signals means that the value from the imaging device is not so sensitive to changes between fractions due to differences in location of the patient and such.

It is to be understood that parts of the radiation beam area may not be used for determining the calibration factor in some cases. For instance if a neck is treated, a part of the beam will pass through the neck and a part may not. The part not passing through the neck will not be included when determining the calibration factor.

With a suitable image analysis program, the user may specify exactly which part of the radiation beam area that the calibration factor is to be based on. The only important thing is that the same area is used both during calibrating fractions using In Vivo dosimetry and subsequent fractions when only the imaging device is used. At one of the first fractions the calibration factor is determined, which factor then is used in subsequent fractions to evaluate, and possibly adjust, the dose level given to the patient.

Even though the detailed description is directed at portal imaging devices as detectors, it is to be understood that other detector means capable of detecting a major part of the radiation beam may be utilized. For instance a CCD-array or an ionization chamber may be placed between the patient and the portal imaging device as a detector means.

It is to be understood that the invention is not limited to the embodiment described and shown on the drawings but may be altered within the scope of the patent claims.

What is claimed is:

1. Method for calibrating a detector means intended for use in an apparatus for radiotherapy, characterised in that it comprises the steps of:

placing a patient in the radiotherapy apparatus with the part of the patient to be treated between a radiation emitting device and the detector means, applying a number of first detectors on the patient, radiating the patient and the first detectors with a beam, measuring the emitted radiation with the first detectors in order to quantify the radiation dose, detecting the radiation emitted and passed through the patient with the detector means, the detector means comprising a plurality of second radiation detectors arranged as to detect the radiation beam, determining the value of the detected radiation from the second detectors of the detector means, and relating the value of the detecting means with the measured radiation dose, thereby quantifying the radiation detected by the detector means.

2. Method according to claim 1, characterised in that a specific area of the whole radiation beam area is chosen, wherein the second detectors in that specific area are used to determine the value of the detected radiation.

3. Method according to claim 1, characterised in that a mean value of the signals from the second detectors of the detector means is determined.

4. Method according to claim 3, characterised in that the detector means is a film capable of capturing radiation, and that the mean value of the density by the radiation is determined.

5. Method according to claim 3, characterised in that the detector means is an electronic image recorder, and that the mean value of the signals from the pixels affected by the radiation is determined.

6. Method according to claim 1, characterised in that the emitted radiation is measured by in vivo dosimetry.

7. Method according to claim 1, characterised in that the detector means is a portal imaging device.

8. Method according to claim 3, characterised in that the relation between the value from the detector means and the measured dose is a factor, hereafter named calibration factor, which is expressed as $$Cal = \frac{D \cdot n}{\sum\limits_{i=1 \to n} S_i}$$

where D is the dose measured by the first detectors, $S_i$ is the signal per pixel or density per area and n is the number of measuring points in the radiation beam area.

9. Use of a detector means in a radiotherapy device, as a quantifier of a dose level emitted from the radiotherapy device, comprising the steps of:

in one fraction placing a patient in the radiotherapy apparatus with the part of the patient to be treated between a radiation emitting device and the detector means, applying a number of first detectors on the patient, radiating the patient and the first detectors with a beam, in one fraction, measuring the emitted radiation with the first detectors in order to quantify the radiation dose, detecting the radiation emitted and passed through the patient with the detector means, the detector means comprising a plurality of second radiation detectors arranged as to detect the radiation beam, determining the value of the detected radiation from the second detectors of the detector means, and relating the value of the detecting means with the measured radiation dose, and in subsequent fractions, using the related value from the detector means to quantify the radiation detected by the detector means.

10. Method according to claim 2, characterised in that in that a mean value of the signals from the second detectors of the detector means is determined.

11. Method according to claim 10, characterised in that the detector means is a film capable of capturing radiation, and that the mean value of the density by the radiation is determined.

12. Method according to claim 10, characterised in that the detector means is an electronic image recorder, and that the mean value of the signals from the pixels affected by the radiation is determined.

13. Method according to claim 4, characterised in that the relation between the value from the detector means and the measured dose in a factor, hereafter named calibration factor, which is expressed as $$Cal = \frac{D \cdot n}{\sum\limits_{i=1 \to n} S_i}$$

where D is the dose measured by the first detectors, $S_i$ is the signal per pixel or density per area and n is the number of measuring points in the radiation beam area.

* * * * *